(12) United States Patent
Ghoreishi

(10) Patent No.: US 8,475,852 B2
(45) Date of Patent: Jul. 2, 2013

(54) TOPICAL THERAPEAUTIC COMPOSITION AND PALLIATIVE TREATMENT METHOD

(76) Inventor: Javad Ghoreishi, Brookline, MA (US)

( * ) Notice: Subject to any disclaimer, the term of this patent is extended or adjusted under 35 U.S.C. 154(b) by 0 days.

(21) Appl. No.: 13/507,719

(22) Filed: Jul. 21, 2012

(65) Prior Publication Data

US 2013/0108724 A1    May 2, 2013

Related U.S. Application Data

(60) Provisional application No. 61/628,217, filed on Oct. 26, 2011.

(51) Int. Cl.
*A01N 65/00* (2009.01)
(52) U.S. Cl.
USPC ......................................................... 424/725
(58) Field of Classification Search
None
See application file for complete search history.

(56) References Cited

U.S. PATENT DOCUMENTS

| | | | |
|---|---|---|---|
| 3,935,310 | A | 1/1976 | Homan |
| 4,761,285 | A | 8/1988 | Vasiliou et al. |
| 5,716,625 | A | 2/1998 | Hahn et al. |
| 6,455,076 | B1 | 9/2002 | Hahn et al. |
| 6,544,530 | B1 | 4/2003 | Friedman et al. |
| 6,582,710 | B2 | 6/2003 | Deckers et al. |
| 7,060,306 | B2 | 6/2006 | Springstead |
| 7,704,518 | B2 | 4/2010 | Tamarkin et al. |
| 7,838,037 | B2 | 11/2010 | Kvitnitsky et al. |
| 7,972,631 | B2 | 7/2011 | Xu |
| 2002/0098210 | A1 | 7/2002 | Hahn et al. |
| 2004/0167479 | A1 | 8/2004 | Warren et al. |
| 2007/0042055 | A1 | 2/2007 | Palpu et al. |
| 2008/0038377 | A1 | 2/2008 | Citow |
| 2009/0208593 | A1 | 8/2009 | Zannini |
| 2011/0067728 | A1 | 3/2011 | Chakrabarty et al. |

*Primary Examiner* — Michael Meller
(74) *Attorney, Agent, or Firm* — Greenblum & Bernstein, P.L.C.

(57) ABSTRACT

Disclosed herein is a topical therapeutic composition and method for the palliative treatment of irritated or inflamed perianal tissue. The therapeutic composition comprises olive oil and tea tree oil. The palliative treatment of the invention involves application of the composition to irritated or inflamed perianal tissue. The composition and method of the invention can be employed in the palliative treatment of such human maladies as hemorrhoids, fissures and pruritis ani.

1 Claim, No Drawings

# TOPICAL THERAPEAUTIC COMPOSITION AND PALLIATIVE TREATMENT METHOD

CROSS-REFERENCE TO RELATED APPLICATION

This application claims the benefit of U.S. Provisional Application Ser. No. 61/628,217, filed by the present applicant on Oct. 26, 2011.

BACKGROUND OF THE INVENTION

The present invention relates broadly to a topical therapeutic composition and is more particularly concerned with a composition which is therapeutically effective when topically applied to irritated or inflamed perianal tissues such as occur in such ano-rectal conditions as hemorrhoids (also known as "piles"), fissures, pruritus ani and the like.

Among the more bothersome conditions of Man are those which involve the irritation or inflammation of the perianal tissue. Not only is the physical discomfort of soreness and burning sensation involved, but also there often occur severe emotional issues and social stigmas attendant the sufferer's almost universal compelling urge to repeatedly scratch and touch the affected area. The more common of these conditions are hemorrhoids, fissures and pruritus ani.

Hemorrhoids are swollen veins in the lower portion of the rectum or anus and usually result from increased intravenous pressure such as can occur during pregnancy, childbirth, sitting for extended periods, excessive straining during defecation and chronic diarrhea or constipation. Internal hemorrhoids occur just inside the anus, but may protrude through the anal opening. External hemorrhoids occur just outside the anal opening. Hemorrhoidal symptoms include itching of or pain in the perianal tissue, particularly when sitting or defecating, the presence of frank blood on toilet tissue or toilet bowl and the presence of tender lumps in the perianal tissue Fissures are simply tears in the anal or perianal tissue, usually brought about by the passage of hard, oversize stools through the anal opening. Pain and bleeding are the usual symptoms of the presence of fissures.

Pruritus ani is a condition characterized by a chronic itching of the perianal tissue of such severity that the afflicted suffer a compelling urge to scratch the affected tissue, often with accompanying burning and soreness. Causatives of this condition are varied, ranging from an excessively moist local environment such as caused by perspiration, to infectious attack, such as in *Candidiasis*. In some people, the intake of irritating foods, such as coffee, tea, carbonated beverages, tomatoes and the like, may cause or at least contribute to the severity of this condition.

In accordance with the invention, I have discovered a composition which, when topically applied to the affected area, functions as a palliative, thereby to sooth and promote healing of irritated or inflamed perianal tissue.

OBJECTS OF THE INVENTION

It is a principal object of the present invention to provide a novel topical therapeutic composition.

It is another object of the invention to provide a novel method for the palliative treatment of irritated or inflamed perianal tissue.

Other objects and advantages of the invention will, in part, be obvious and will, in part, appear hereinafter.

SUMMARY OF THE INVENTION

The topical therapeutic composition of the invention broadly comprises olive oil and between about 0.001 to about 10% by volume of tea tree oil. I generally prefer a composition wherein the concentration of the tea tree oil component is about 5% by volume.

The palliative treatment method of the invention comprises applying the composition of the invention to irritated or inflamed perianal tissue.

DETAILED DESCRIPTION OF THE INVENTION

Olive oil is the extract of the olive (*Olea europaea*) and is generally produced by first grinding the ripe olive fruit into a paste and then extracting the oil from the ground paste by mechanical or chemical means, In general, for the composition of the invention I prefer an olive oil component which is derived from the ground paste solely by mechanical means (virgin olive oil), such as by pressing or centrifugation.

Due to its chemical makeup and physical properties the olive oil component of the invention contributes meaningfully to the overall palliative therapeutic effect achieved by the composition of the invention when applied topically to an irritated or inflamed perianal tissue. For instance, its oily consistency permits it to act as a lubricant and to thereby reduce the pain and itching associated with this condition. Too, its oleophilic nature acts as a barrier to water which is highly desirable to promote healing of irritated and/or inflamed perianal tissue. Too, its mildly acidic $p^H$ roughly matches the $p^H$ of healthy perianal tissue and thus serves to maintain this normal condition of acidity, thereby also fostering the healing process. Additionally, olive oil contains substantial amounts of antioxidants and vitamins, particularly vitamins A, E and K, and all of which can contribute substantially to the nourishment of the perianal epithelium as it undergoes the healing process.

Tea tree oil is the oily extract produced commercially by distillation of tea tree (*Melaleuca alternafolia*) plant material and, to a lesser extent, by distillation of *Melaleuca dissitiflora* or *Melaleuca linarafolia* plant materials. Tea tree oil has very substantial antiviral, antibacterial, antifungal and antiseptic properties and it is these properties which serve in the composition of the invention to minimize infectious attack on the perianal tissue as it heals. Thus, the components of the composition of the invention cooperate to provide a salubrious environment whereby the healing process of the perianal tissue can proceed at maximum pace and with minimum risk of secondary infection.

In use the therapeutic composition of the invention, as previously mentioned, is topically applied to the affected inflamed perianal tissue. This can be done by direct digital manipulation or by use of pledgets, gauze pads, cotton balls and the like saturated with the composition. Also contemplated is the use of various applicator devices known in the art. In the treatment of internal hemorrhoids a felted tampon can be saturated with the composition of the invention and then inserted into the anal canal. In addition, by blending with appropriate thickening agents, such as fumed silica, the composition of the invention can be converted to a form stable solid, suitable for conformation into a suppository shape and used as such.

The therapeutic composition of the invention, in addition to its olive oil and tea tree oil components, can also comprise additional medicaments and modifiers. For instance, the basic olive oil/tea tree oil composition can be physically modified by emulsifying it with an aqueous phase, thereby to result in a composition having the physical form of a lotion, salve, cream or the like. Too, additional medicaments can be dissolved into the oil phase or, if present, the aqueous phase of the composition. Exemplary of such additional suitable medicaments are one or more of the following: local anesthetics such as benzocaine, pramocaine, lidocaine or tetracaine; vasoconstrictors such as ephedrine sulfate or phenylephrine; protectants such as aluminum hydroxide, cocoa butter, kaolin, lanolin, zinc oxide or cod liver oil; astringents such as witch hazel; analgesics such as *Aloe vera* and corticosteroids such as hydrocortisone and methylprednisolone.

Although the invention has been described and illustrated above with respect of certain specific embodiments thereof it should be recognized and understood that various alterations and modifications in the details of composition and use may be made without departing from the essential spirit and scope of the invention as indicated by the appended claims.

The invention claimed is:

1. A topical composition comprising for treating hemorrhoids consisting essentially of therapeutically effective amounts of olive oil, tea tree oil and aluminum hydroxide.

\* \* \* \* \*